United States Patent [19]

Townsley

[11] Patent Number: 4,745,058

[45] Date of Patent: May 17, 1988

[54] METHOD FOR PRODUCING CELLULOSIC FIBERS AND MICROCRYSTALLINE CELLULOSE

[76] Inventor: Philip M. Townsley, 4569 W. 13th Avenue, Vancouver, B. C., Canada, V64 2V5

[21] Appl. No.: 608,892

[22] Filed: May 10, 1984

[51] Int. Cl.$^4$ .................... C12P 19/04; C12R 1/02
[52] U.S. Cl. .................... 435/101; 435/262; 435/267; 435/274; 435/277; 435/278; 435/813; 435/823; 210/498
[58] Field of Search .............. 435/101, 262, 267, 274, 435/277, 813, 823, 278; 210/498

[56] References Cited

U.S. PATENT DOCUMENTS 3,277,814 10/1966 Malm et al. .................. 210/498
3,970,549 7/1976 Ennis et al. .................. 210/498

FOREIGN PATENT DOCUMENTS 0580595 9/1946 United Kingdom .............. 435/101

OTHER PUBLICATIONS

Muhlethaler, Kurt, "The Structure of Bacterial Cellulose", Biochimica et Biophysica Acta, vol. 3 (1949), pp. 527–535.
Joseph, M., "Mercerization", Introductory Textile Science, 1977, p. 304.

Primary Examiner—Charles F. Warren
Assistant Examiner—Elizabeth A. Hanley
Attorney, Agent, or Firm—Christensen, O'Connor, Johnson & Kindness

[57] ABSTRACT

Cellulose strands are produced by causing a growing medium containing *Acetobacter xylinum* to flow along a straight-line path over a growing surface. Cellulose fibrils produced by the bacteria arrange themselves in strands on the growing surface. These strands can be converted into threads and/or yarns. The cellulose fibrils produced by *Acetobacter xylinum* can also be converted to microcrystalline cellulose.

10 Claims, No Drawings

METHOD FOR PRODUCING CELLULOSIC FIBERS AND MICROCRYSTALLINE CELLULOSE

BACKGROUND OF INVENTION

The present invention relates to a method of producing cellulose from bacterial cultures that are members of the genus Acetobacer, and more particularly to a method for making fibers from cellulose produced by such bacterial cultures and to a method for making microcrystalline cellulose from cellulose produced by such bacterial cultures.

Bacteria of the genus Acetobacter, and particularly the gram negative bacterium *Acetobacter xylinum* is capable of synthesizing a fibril of cellulose. The ribbonlike fibrils are generated generally at the gas-liquid interface of a standing culture. Randomly intertwining ribbons of cellulose fibrils produce a thick membrane commonly referred to as a pellicle. These cellulosic pellicles have a relatively high tensile strength.

SUMMARY OF THE INVENTION

The present invention has two aspects. The first aspect relates to a method for producing cellulose fibers comprising the steps of placing cellulose fibril producing bacteria of the genus Acetobacter in a growing medium, causing the growing medium to flow over a growing surface in a straight-line flow path, and allowing the bacteria to produce cellulose fibrils that become intertwined to form a fibrous strand that is generally oriented parallel to the medium flow path. These fibrous strands can be directly interwoven into a useful fiber or yarn.

The second aspect of the present invention relates to a method for producing microcrystalline cellulose comprising the steps of generating the cellulose fibers by placing a cellulose fiber producing bacteria of the genus Acetobacter in a growing medium. The cellulose fibrils produced by the bacteria are then removed from the medium and excess medium is removed from the fibrils. The fibrils are then immersed in an aqueous solution of a base for a predetermined period of time after which the fibrils are neutralized by immersing the fibrils in an acidic solution. The fibrils are thereafter subjected to a treatment with a hot strong acid and are disintegrated to produce microcrystalline cellulose.

DETAILED DESCRIPTION OF THE INVENTION

In its first aspect, the present invention provides a method for producing strands of cellulose that can be directly processed into useable yarns and threads. The cellulose itself is produced by cellulose producing bacterial cultures of the genus Acetobacter, including *A. xylinum* and *A. acetigenum*. Bacteria of the specie *Acetobacter xylinum* are most effective. While this species of bacteria tends to mutate, all members of the species produce cellulose fibrils, although in varying amounts. Thus, it is most preferred that the members of the species that are highest in cellulose production be chosen for use in connection with the present invention. These members can be selected in accordance with procedures readily available in the art.

In accordance with the present invention, the bacteria are placed in a growing medium. Any suitable growing medium known in the art can be utilized, for example, an aqueous sucrose containing medium is satisfactory. The medium should include a nitrogen source for the bacteria. Peptones provide a suitable nitrogen source for the bacteria. A yeast extract may be included in the growing medium to provide the necessary vitamins for the bacteria. An antibiotic such as sorbic acid may also be required to control the yeast and mold. A typical artificial growing medium can contain, for example, up to 10 percent sucrose, up to about 0.05 percent potassium sorbate (or other suitable source of sorbic acid), approximately 0.4 percent acetic acid, up to approximately 0.25 percent of yeast extract, and up to about 0.5 percent of bacto-peptone. The acetic acid is included to adjust the pH to about 4.0 to 4.5 which optimizes growing conditions for the *A. xylinum* while discouraging undesirable bacterial contamination. With this medium an innoculum of about 10 percent v/v three day old *A. xylinum* can be employed. Other conventional growing mediums can be utilized as desired. In addition, natural growing mediums such as pineapple or coconut juice can also be effectively employed.

The cellulose strands are produced in accordance with the present invention by causing the bacteria laden growing medium to flow over a growing surface along a straight-line path. The cellulose fibrils produced by the bacteria tend to string out along the flow path direction and intertwine to form strands of fibrils. These strands can be periodically removed from the growing surface, treated as described below, and woven or otherwise made into thread or yarn by conventional procedures.

The bacterial laden growing medium can be caused to flow in a straight-line flow path by a variety of mechanical techniques. One technique is to prepare a ramp having a plurality of v-shaped grooves that run down the ramp. The ramp is inclined at a relatively low pitch so that growing medium placed at the top of the ramp adjacent the grooves flows slowly down the grooves to the bottom. The growing medium can then be collected and recirculated to the top of the ramp. The fibrils produced by the bacteria tend to string out along the direction of the grooves and become intertwined along the bottom and sides of the grooves. Periodically the strands can be removed and further processed as described below. A suitable ramp for the production of strands can have a flow path length of approximately 2½ feet, width of approximately 1½ feet and a height at its upper end of about 2 inches. This provides a pitch of about fifteen to one. Each of the v-shaped grooves have sides that are approximately ⅛ inch long. The width across the upper ends of the grooves is approximately ⅛ inch. Alternatively, the bacterial laden growing medium can be dripped down a string or fiber of material that can later be dissolved or removed. When this alternative is employed, cellulose strands are produced that have a hollow core, which is a structure similar to naturally occurring cotton.

The rates at which the bacterial laden growing medium are caused to flow down the grooves or down a mandrel are not critical. While it is preferred to cause the growing medium to intermittently flow along its flow path, continuous flow can be utilized if desired. For example, the growing medium can be caused to flow down a ramp as described above for one hour periods at one hour intervals. The temperature of the growing medium should be maintained at an optimum temperature for bacterial growth of about 25° C. to about 28° C., although the temperatures can vary from about 20° C. to about 35° C. Toward the end of this broader range, however, the cellulose production rate is significantly reduced. At the preferred temperatures, a cellulose strand on the order of one to two millimeters in thickness is produced utilizing the grooved ramp approach in approximately one week.

Once a strand of this size is grown, the strands can be removed from the growing surface and rinsed with water to remove some of the bacterial laden growing medium.

The cellulose strands are then mercerized. This mercerization is generally conducted in accordance with standard procedures. The mercerization does change the physical structure to increase the flexibility and strength of the fiber. Moreover, the mercerization steps sterilize the fiber and extracts residual microbial protein. Mercerization is conducted in an aqueous medium containing a strong base such as sodium or potassium hydroxide. It is preferred that the base be present in an amount ranging from about 5 percent to about 15 percent by weight based on the solution. The mercerization is conducted at temperatures ranging from 50° C. to 65° C. for a period of time up to about 1 hour, preferably from about 15 to 45 minutes. The most perferred mercerization solution comprised an 8.3 percent by weight solution of sodium hydroxide. The preferred mercerization temperature and time are 57° and 27 minutes, respectively.

Once the cellulose strands have been mercerized, they are washed in the water. The excess water is then removed from the fibers and the fibers are dried utilizing a hot air stream to ambient dryness. Glycerol can be used to improve fiber flexibility. Conventional clothes or fiber drying temperatures and tumbling techniques can be employed. Thereafter, the fibers can be spun or woven into yarns and/or threads.

Tests have indicated that the tensile strength of the unmercerized strands produced in accordance with the invention have a tensile strength on the order of 30,138 g/mm$^2$. Mercerized strands produced in accordance with the invention have a tensile strength on the order of 83,992 g/mm$^2$. For comparison, mercerized commercial cotton has a typical tensile strength of about 69,900 g/mm$^2$.

In its second aspect, the present invention provides a method for producing microcrystalline cellulose from the cellulose fibrils produced by bacteria of the genus Acetobacter, and especially those belonging to the species *A. xylinum*.

In this aspect of the invention, cellulose pellicles are produced in accordance with techniques similar to those set forth above. However, instead of causing the bacterially laden growing medium to flow over a growing surface along a straight-line path, no movement of the growing medium is necessary. Instead, cellulose pellicles are grown adjacent the surface of standing growing medium. The cellulose pellicles can be grown in trays 1 feet by 3 feet having relatively high sides. The depth of the medium in the trays can typically be on the order of 1½ to 2 inches. Once a pellicle of fibrils is built up to a thickness of about 1 inch it is removed. A substantial amount of growing medium still remains in the mat. The excess growing medium is squeezed or otherwise mechanically removed from the mat by, for example, running it through a pair of closely spaced rollers. This partially dried mat is then washed with water and the excess water again squeezed from the mat. The rinsed mat is then ground or comminuted into small particles. A high shear grinder such as those made by Waring should be employed to break the fibrils into small particles. It has been found that a pellicle having a volume of approximately 0.5 liters can be suitably ground to an average particle size of 2 millimeters by placing it in a 1 liter Waring blender having a rating of 115 volts and 5 to 7 amps and operated at top speed. By turning the Waring blender off and on with very short pulses and allowing the blender to run for approximately one-half second during each pulse, the material is turned into a pulp in approximately 1 minute. The average strand length is approximately 2 millimeters The ground material is then subjected to a treatment in a relatively strong base to clean the material, to extract any excess medium, and to remove any bacterial residue. Strong bases such as sodium hydroxide and potassium hydroxide are suitable for this treatment. Sodium hydroxide can, for example, be present in an amount ranging from 5 to 15 percent by weight based on the total solution. The ground fibers can be immersed in the sodium hydroxide solution for up to three hours with slow agitation. The solution is maintained at room temperature. Excess solution is removed by filtering the fibers over a sintered glass filter having a coarse or medium pore size. Vacuum suction can be applied to the filter if desired.

Thereafter, the fibers can again be washed to remove the remaining sodium hydroxide solution and to lower the pH of the fibers. Thereafter, the fibers are neutralized in a weak acidic solution. An acetic acid solution containing from 1 percent to 5 percent acetic acid in water is suitable for neutralization purposes. The acid bath utilized in this neutralization should be sufficiently weak so that substantially no hydrolysis occurs. After the fibers have been subjected to the acid neutralization for up to about 1 hour, excess acid solution is squeezed from the fibers and there again washed in a water bath. Thereafter the cellulose fibers are bleached in sodium chlorite. Bleaching is carried out at 70° C. for three hours. This bleaching is carried out in accordance with the teachings of L. E. Wise, M. Murphy, and A. A. DAddieco, 1946. A Paper Trade Journal, Volume 122, pages 35 to 43. "Chlorite Holocellulose: Its Fractionation and Bearing on Summative Wood, Analysis and Studies on the Hemicullulose", expressly integrated herein by reference.

Thereafter, the fibers are subjected to a strong acid hydrolyzation step by immersing the fibers for 15 minutes in a 2.5 N hydrochloric acid solution maintained at about 100° C. The fiber is then filtered, washed, neutralized, again washed, disintegrated and dried to produce microcrystalline cellulose. The procedure beginning with the strong acid hydrolyzation is described by O. A. Battista in an article entitled "Microcrystalline Cellulose", taken from *Cellulose and Cellulose Derivatives*, Volume 5, edited by Norbert M. Bikales and L. Segal; Wiley Publishing Company, 1971 pages 1269 through 1271, expressly incorporated herein by reference.

Thus the present invention in its second aspect provides a method for producing bacterial cellulose, and treating that bacterial cellulose so that it can be hydrolyzed and converted into microcrystalline cellulose in accordance with known procedures.

While the present invention has been described in relation to preferred embodiments, one of ordinary skill will be able to effect various changes and substitutions of equivalents and make other alterations without departing from the broad concepts disclosed herein. It is therefore intended that the scope of protection provided by Letters Patent hereon be limited only by the definition contained in the appended claims and equivalents thereof.

The embodiments of the invention in which an exclusive property or privilege is claimed are defined as follows:

1. A method for producing cellulose strands comprising the steps of:

placing cellulose fibril producing bacteria of the genus Acetobacter in a growing medium, flowing said growing medium over a surface adapted to direct said growing medium in a straight-line flow path and to allow cellulose fibrils produced by the bacteria to string out along the flow path and intertwine to form a cellulose strand, and thereafter removing said cellulose strand from said surface.

2. The method of claim 1 wherein said surface comprises a plurality of troughs oriented parallel to each other and sloped so as to provide a straight-line flow path for said medium, said medium flowing from one end of said troughs to the other end of said troughs.

3. The method of claim 1 wherein said growing medium is maintained at a temperature of from 20° to 35° C.

4. The method of claim 3 wherein said growing medium is maintained at a temperature on the order of from 25° to 28° C.

5. The method of claim 1 wherein said growing medium flow is continuous.

6. The method of claim 1 wherein said flow is intermittent.

7. The method of claim 1 wherein said growing medium comprises an aqueous sugar solution and a nitrogen source.

8. The method of claim 7 wherein said growing medium further comprises a yeast extract and an antibiotic.

9. The method of claim 1 further comprising the step of:

immersing said cellulose strand in a bath comprising an aqueous solution of a strong base while maintaining the temperature of said solution in the range of from 50° C. to 65° C.

10. The method of claim 1 wherein the bacteria is selected from the group consisting of *Acetobacter xylinum* or *Acetobacter acetigenum*.

* * * * *